United States Patent
Kohl et al.

(10) Patent No.: US 10,940,136 B2
(45) Date of Patent: Mar. 9, 2021

(54) CANNABINOIDS FOR PROPHYLACTIC TREATMENT OF INVOLUNTARY WEIGHT LOSS

(71) Applicant: AOP ORPHAN PHARMACEUTICALS AG, Vienna (AT)

(72) Inventors: Agnes Kohl, Vienna (AT); Ralf Lenhard, Vienna (AT)

(73) Assignee: AOP ORPHAN PHARMACEUTICALS AG, Vienna (AT)

( * ) Notice: Subject to any disclaimer, the term of this patent is extended or adjusted under 35 U.S.C. 154(b) by 0 days.

(21) Appl. No.: 16/464,247

(22) PCT Filed: Nov. 24, 2017

(86) PCT No.: PCT/EP2017/080353
§ 371 (c)(1),
(2) Date: May 24, 2019

(87) PCT Pub. No.: WO2018/096100
PCT Pub. Date: May 31, 2018

(65) Prior Publication Data
US 2019/0388383 A1    Dec. 26, 2019

(30) Foreign Application Priority Data

Nov. 24, 2016    (EP) .................................... 16200498

(51) Int. Cl.
| | | |
|---|---|---|
| *A61K 31/352* | (2006.01) | |
| *A61P 3/04* | (2006.01) | |
| *A61P 35/00* | (2006.01) | |
| *A61K 9/00* | (2006.01) | |
| *A61K 45/06* | (2006.01) | |

(52) U.S. Cl.
CPC .......... *A61K 31/352* (2013.01); *A61K 9/0002* (2013.01); *A61K 9/0053* (2013.01); *A61K 45/06* (2013.01); *A61P 3/04* (2018.01); *A61P 35/00* (2018.01)

(58) Field of Classification Search
CPC .. A61K 2300/00; A61K 31/05; A61K 31/164; A61K 31/352; A61K 31/473; A61K 31/5375; A61K 31/7068; A61K 33/24; A61K 45/06; A61K 9/0002; A61K 9/0053; A61P 21/00; A61P 35/00; A61P 3/04; A61P 43/00

See application file for complete search history.

(56) References Cited

FOREIGN PATENT DOCUMENTS

| EP | 2643022 B1 | 7/2018 |
|---|---|---|
| GB | 2450493 A | 12/2008 |

OTHER PUBLICATIONS

Meiri et al. (Current Medical Research and Opinions, vol. 23 (3), 2007 533-543 (Year: 2007).*
Chang et al. (Annals of internal Medicine 1979, 91:819-824) (Year: 1979).*
Argiles et al, "The cachexia score (CASCO): a new tool for staging cachectic cancer patients", 2011, J Cachexia Sarcopenia Muscle, vol. 2, pp. 87-93.
Blauwhoff-Buskermolen et al, "Loss of Muscle Mass During Chemotherapy Is Predictive for Poor Survival of Patients With Metastatic Colorectal Cancer", 2016, J Clin Oncol, vol. 34, No. 12, pp. 1339-1344.
Brierley et al, "Therapeutic Potential of Cannabigerol for Chemotherapy-Induced Cachexia", 2016, Appetite, vol. 101, pp. 221.
Blum et al, "Validation of the Consensus-Definition for Cancer Cachexia and evaluation of a classification model—a study based on data from an international multicentre project (EPCRC-CSA)", 2014, Annals of Oncology, vol. 25, No. 8, pp. 1635-1642.
Douglas et al, "Towards a simple objective framework for the investigation and treatment of cancer cachexia: The Glasgow Prognostic Score", 2014, Cancer Treat Rev, vol. 40, No. 6, pp. 685-691.
Fearon et al, "Definition and classification of cancer cachexia: an international consensus", 2011, Lancet Oncol, vol. 12, No. 5, pp. 489-495.
Gorter, R.W. "Erfahrungen mit Dronabinol (Tetrahydrocannbinol) bei onkologischen Patienten mit Anorexie-Kachexie-Syndrom", 2004, Schmerz, vol. 18, suppl. 2, pp. 31-33.
Malik et al, "The Role of Cannabinoids in Regulation of Nausea and Vomiting, and Visceral Pain", 2015, Curr Gastroenterol Rep, vol. 17, No. 2, pp. 429.
Martin et al, "Cancer Cachexia in the Age of Obesity: Skeletal Muscle Depletion Is a Powerful Prognostic Factor, Independent of Body Mass Index", 2013, J Clin Oncol, vol. 31, No. 12, pp. 1539-1547.
Martin et al, "Diagnostic Criteria for the Classification of Cancer-Associated Weight Loss", 2015, J Clin Oncol, vol. 33, No. 1, pp. 90-99.
Di Marzo et al, "Plant, Synthetic, and Endogenous Canniminoids in Medicine", 2015, Annual Review of Medicine: Selected Topics in the Clinical Sciences, vol. 57, pp. 553-574.
Plasse et al, "Recent Clinical Experience With Dronabinol", 1991, Pharmacol. Biochem. and behavior Elsevier, vol. 40, No. 3, pp. 695-700.
Rocha Lima et al, "Irinotecan Plus Gemcitabine Results in No Survival Advantage Compared With Gemcitabine Monotherapy in Patients With Locally Advanced or Metastatic Pancreatic Cancer Despite Increased Tumor Response Rate", 2004, J Clin Oncol, vol. 22, No. 18, pp. 3776-3783.

(Continued)

*Primary Examiner* — Savitha M Rao
(74) *Attorney, Agent, or Firm* — Loza & Loza, LLP; Michael F. Fedrick

(57) ABSTRACT

The present invention provides a new use for cannabinoids in the prevention of pre-cachexia or cachexia in a patient suffering from cancer, wherein said cannabinoid is administered at low dosage and wherein administration is started prior to chemotherapy and is maintained for at least the duration of the chemotherapy.

18 Claims, No Drawings

(56) References Cited

OTHER PUBLICATIONS

Tan et al, "Sarcopenia in an Overweight or Obese Patient Is an Adverse Prognostic Factor in Pancreatic Cancer"; 2009, Clin Cancer Res, vol. 15, No. 22, pp. 6973-6979.
Thoresen et al, "Nutritional status, cachexia and survival in patients with advanced colorectal carcinoma. Different assessment criteria for nutritional status provide unequal results"; 2013, Clinical Nutrition, vol. 32, No. 1, pp. 65-72.
Vigano et al, "The Cachexia Clinic: From Staging to Managing Nutritional and Functional Problems in Advanced Cancer Patients", 2012, Crit Rev Oncog, vol. 17, No. 3, pp. 293-304.
International Search Report for PCT/EP17/80353 dated Feb. 6, 2018; 6 pages.
Written Opinion of the International Searching Authority for PCT/EP17/80353 dated Feb. 6, 2018; 5 pages.
International Preliminary Report on Patentability for PCT/EP17/80353 dated May 28, 2019; 6 pages.
European Extended Search Report for Serial No. 16200498.0 dated Apr. 20, 2017; 8 pages.

\* cited by examiner

CANNABINOIDS FOR PROPHYLACTIC TREATMENT OF INVOLUNTARY WEIGHT LOSS

CROSS-REFERENCE TO RELATED APPLICATIONS

This application is the U.S. national stage of International Patent Application No. PCT/EP2017/080353, filed on Nov. 24, 2017 and entitled CANNABINOIDS FOR PROPHYLACTIC TREATMENT OF INVOLUNTARY WEIGHT LOSS, which claims the benefit of priority under 35 U.S.C. § 119 from European Patent Application No. 16200498.0, filed Nov. 24, 2016. The disclosures of the foregoing applications are incorporated herein by reference in their entirety.

FIELD OF THE INVENTION

The present invention provides a new use for cannabinoids at low dosage in the prevention of pre-cachexia or cachexia in a patient suffering from cancer, wherein administration is started prior to chemotherapy and is maintained for at least the duration of the chemotherapy.

BACKGROUND OF THE INVENTION

Cachexia is a wasting syndrome associated with chronic diseases such as cancer, chronic obstructive pulmonary disease (COPD), sepsis, or chronic heart failure. According to a consensus, the cachectic syndrome is defined as a complex metabolic multifactorial syndrome associated with underlying illness and characterized by loss of skeletal muscle mass with or without loss of fat mass that cannot be fully reversed by conventional nutritional support and leads to progressive functional impairment (Argiles J M. et al., J Cachexia Sarcopenia Muscle 2011, 2:87-93, Fearon K. et al., 2011, Lancet Oncol., 12, 489-95). Cachexia is commonly characterized by weight loss exceeding 5% within the previous 3-12 months or weight loss >2% within the last 6 months and a body mass index (BMI) of <20 kg/m$^2$, combined with fatigue, loss of skeletal muscle, and biochemical abnormalities (e.g., anemia or insulin resistance) (Blum D. et al., 2014, Annals of Oncology, 25, 1635-1642). Cancer-induced cachexia (CIC) is experienced by up to 80% of patients with advanced stage cancer, particularly those with gastrointestinal, pancreatic, thoracic and head and neck malignancies. Despite interventions such as total parenteral nutrition (complete daily intravenous nutrition), anti-inflammatory medications, and anabolic stimulation, patients with cancer-induced cachexia continue to lose weight and often become so frail that they are unable to receive anti-cancer therapies. This distinguishes CIC from other forms of cachexia, which may respond to nutrition supplementation coupled with anti-inflammatory therapy.

According to the consensus, the term "pre-cachexia" is a condition associated with no or very small weight loss (less than 5% of body weight loss in 6 months) which is associated with underlying chronic disease and characterized by inflammation, and/or metabolic alterations.

The development of new oncologic therapies has transformed many cancers into chronically managed diseases. However, the efficacy of these new treatment regimens does not guarantee an increase in survival. While surgery, radiation or chemotherapy can reduce tumor size, this reduction does not always correlate with an increase in survival. In fact, for many patients, the degree of tumor burden does not correlate with prognosis. The difference in survival time for patients with only modest tumor burden is only about eight months more than the survival time of patients with extensive tumor burden. This result may be attributed, at least in part, to cachexia. The clinical manifestations of cachexia are complex: muscle and fat wasting, multi organ dysfunction (e.g., cardiac, pulmonary, gastrointestinal), and profound metabolic derangement.

More than 25% of cancer deaths are not caused by cancer but by cachexia. Cachexia associated deaths include death by respiratory failure, cardiac failure, and metabolic derangement.

While cachexia shares certain phenotypic similarities with food deprivation, in fact cachexia is distinct from starvation. Even where patients with cachexia are provided with total parenteral nutrition, weight loss, including loss of lean body mass, continues. These losses have proven refractory to all therapeutic interventions, except for a complete removal of the cancer, which remains elusive for the vast majority of cancer patients.

In general, several proposals for the classification of patients into cachexia stages have been made. The first, the Cachexia Score (CASCO) weights and sums five different factors: body weight and lean body mass loss, inflammatory, immunological and metabolic disturbances, physical performance and quality of life (Argiles J M. et al., J Cachexia Sarcopenia Muscle 2011, 2:87-93).

CASCO is for example calculated as follows by Argiles et al., 2011:

Body weight loss and composition, BWC (0-40)
+inflammation/metabolic disturbances/immunosuppression, IMD (0-20)
+physical performance, PHP (0-15)
+anorexia, ANO (0-15)+quality of life, QDL (0-10),
wherein: 0-25 is mild, 25-50 is moderate, 50-75 is severe ad 75-100 is terminal phase (Argiles et al., 2011).

Vigano et al. (Crit Rev Oncog 2012, 17:293-304) classified the patients into three cancer cachexia stages by two independent researchers according to different combinations of clinical criteria and biological measurements. Patients were categorized as being non-cachectic, being pre-cachectic, being cachectic, and being in refractory cachexia.

A further classification is the modified Glasgow prognostic score to specify the severity of cachexia and accompanying inflammatory processes (Douglas E. and McMillan D. C., 2014, Cancer Treatment Reviews, 40, 685-691).

The Glasgow prognostic score (GPS) is determined as follows:
GPS=0, i.e. no cachexia: albumin >35 g/l, C-reactive protein (<10 mg/l); weight loss uncommon—no metabolic upset.
GPS=1, i.e. pre-cachexia: albumin >35 g/l, C-reactive protein (>10 mg/l), weight loss uncommon—metabolic upset
GPS=2, i.e. refractory cachexia: albumin <35 g/l, C-reactive protein (>10 mg/l), weight loss common—metabolic upset.

Gorter R. W. (SCHMERZ, 2004, vol. 18, suppl. 2, pp. 31-33) report the use of dronabinol in cancer patients with anorexia cachexia of more than 2.5 mg per day.

Plasse T. F. et al. (Pharmacology Biochemistry and Behavior, Elsever, US, vol. 20, no. 3, 1991, pp. 695-700) describes the use of dronabinol in patients receiving cancer therapy.

GB 2 450 493 A discloses cannabigerol for treatment of cachexia.

Brierley D. I. et al. (Appetite, vol. 101, 2016, page 221) reports the potential of cannbigerol for chemotherapy induced cachexia.

The use of cannabinoids in medicine is described by Marzo Di Vincenzo et al. (Annual Review of Medicine: Selected Topics in the Clinical Sciences, vol. 57, 2005, pp. 553-574).

Despite being common in many solid tumor cancers, cachexia remains a largely untreated complication that predisposes patients to an increased mortality. Treatment approaches for CIC, including anabolic steroids, anti-catabolic therapies, appetite stimulants, and nutritional interventions, have failed to show significant efficacy. In fact, once established, no therapeutic approach has been able to reverse cancer-induced cachexia.

Accordingly, there is an urgent and unmet need for providing methods of treating patients before they meet the clinical criteria for pre-cachexia or cachexia, i.e., when they do not show any signs of cachexia or when they are pre-cachectic, so that the patient's entry into pre-cachexia is prevented or progression from pre-cachexia to cachexia is disrupted.

SHORT DESCRIPTION OF THE INVENTION

The need is solved by the embodiments of the invention.

The present invention provides a new treatment regimen for preventing the onset of pre-cachexia or cachexia in subjects suffering from a chronic disease like cancer.

The invention provides a novel method for inhibiting the emergence of pre-cachexia in a subject being at risk of pre-cachexia by administering a cannabinoid.

The invention further provides a novel method for inhibiting the progression of pre-cachexia to cachexia in a subject by administering a cannabinoid.

This invention specifically provides a method of treating, reducing the severity of, reducing the incidence of, delaying the onset of, or reducing pathogenesis of pre-cachexia, early cachexia or cachexia in a subject.

The present invention provides a cannabinoid for use in the prophylactic treatment of pre-cachexia or cachexia in a patient suffering from cancer by administering low doses of a cannabinoid or mixtures of cannabinoids, wherein the administration is started prior to chemotherapy and is maintained for at least the duration of the chemotherapy.

According to an embodiment of the invention, the cannabinoid is supplementally administered in conjuction with chemotherapeutic treatment. The supplemental treatment begins prior to an initial conventional cancer treatment, and at least continues into the interval between subsequent treatments.

Specifically, there is provided a cannabinoid for use in the prophylactic treatment of pre-cachexia or cachexia of a patient suffering from cancer, wherein said cannabinoid is administered in an amount of 0.1 mg to 20 mg/day, specifically in an amount of 0.25 mg to 5 mg/day and administration is started prior to chemotherapy and is maintained for at least the duration of the chemotherapy.

It was surprisingly shown by the inventors that administration of low doses of up to 20 mg/day and even very low doses of up to 5 mg/day during cancer therapy resulted in significant prevention of the onset of pre-cachexia and cachexia.

According to an embodiment of the invention, the cannabinoid is selected from natural, modified or synthetic cannabinoids, specifically it is selected from the group of cannabidiol (CBD), 9-tetrahydrocannabinol, 8-tetrahydrocannabinol, (+)-1,1-dimethylheptyl analog of 7-hydroxy-delta-6-tetrahydrocannabinol, 3-(5'-cyano-1,1'-dimethyl-pentyl)-1-(4-N-morpholinobutyryloxy) delta 8-tetrahydrocannabinol hydrochloride, dexanahinol, nabilone, levonantradol, N-(2-hydroxyethyl) hexadecanamide, delta-8-tetrahydrocannabinol or, any active metabolite, derivative or analogue thereof.

In a preferred embodiment of the invention, nabilone is used for prophylactic treatment of pre-cachexia or cachexia.

According to a specific embodiment of the invention, the cannabinoid is administered prior to the onset of pre-cachexia or cachexia.

According to a further embodiment, administration of the cannabinoid is commenced once the subject has been diagnosed with cancer or metastatic cancer.

According to a specific embodiment, the cannabinoid is administered during chemotherapy.

According to a specific embodiment, administration of the cannabinoid is continued once the chemotherapy treatment has been suspended or terminated.

According to a specific embodiment, the cannabinoid is formulated for oral, inhalative or subcutaneous delivery.

According to a specific embodiment, the oral formulation is in the form of a tablet, a capsule, a sachet, sprinkles, or a suspension.

According to a further embodiment, the cannabinoid is formulated as a slow release formulation.

According to a further embodiment, the inhalation formulation is in the form of a spray, liquid, emulsion or dry powder.

According to a further embodiment, the patient suffers from metastatic cancer.

In a further aspect, the cancer is selected from the group consisting of prostate cancer, breast cancer, small cell lung carcinoma, non-small cell lung carcinoma, colon cancer, rectum cancer, bladder cancer, kidney cancer, leukemia, mouth cancer, esophagus cancer, larynx cancer, stomach cancer, melanoma, pancreatic cancer, endometrial cancer, uterine sarcoma, ovarian cancer, testicular cancer, multiple myeloma, brain tumor, thyroid cancer, Hodgkin's lymphoma, non-Hodgkin's lymphoma, liver cancer, gastric cancer, sarcoma, osteosarcoma, acute non-lymphocytic leukemia, skin cancer, cancer of the musculoskeletal system, head and neck cancer and glioma.

According to an embodiment of the invention, the cannabinoid is used for prophylactic treatment of pre-cachexia which is specifically characterized by a patient's weight loss of >1 kg and <5% compared to the weight before start of chemotherapy treatment cycle.

According to an embodiment of the invention, the cannabinoid is used for the prophylactic treatment of cachexia which is specifically characterized by a weight loss of >5% of the patient compared to the weight before start of a chemotherapy treatment cycle.

In yet a further embodiment, the patient further suffers from one or more of following conditions:
 a) progressive loss of both fat and skeletal muscle,
 b) refractoriness of weight loss to increased nutritional input,
 c) elevated resting energy expenditure (REE),
 d) decreased protein synthesis,
 e) altered carbohydrate metabolism,
 f) hyper-catabolism of muscle via the ATP-ubiquitin-proteasome pathway of proteolysis,
 g) increased degradation of adipose tissue via lipolysis,
 h) asthenia,
 i) anemia, j) chronic fatigue,
k) nausea, or
l) loss of bone mass.

The invention further provides a method wherein administration of a cannabinoid starts immediately after first diagnosis of cancer or immediately after diagnosis of relapse of cancer disease.

According to an embodiment of the invention, administration starts at least 1, 2, 3, 4, 5, 6, 7, 8, 9, 10, 11, 12, 13, 14, 15, 16, 17, 18, 19, 20, 21 days, or at least 1 week, preferably at least 2 weeks, preferably at least 3 weeks before chemotherapy.

According to an embodiment of the invention, the cannabinoid is administered from the beginning until the end of a complete chemotherapy treatment and optionally up to 12 months after termination of chemotherapy.

In a specific embodiment, due to the treatment according to the present invention, the weight loss of the patient after one chemotherapy treatment cycle is less than 15%, specifically less than 10%, specifically less than 5%, specifically less than 2.5%, specifically less than 2%, specifically less than 1% compared to the weight before start of chemotherapy treatment cycle.

In a specific embodiment, due to the treatment according to the present invention, the Glasgow prognostic score is kept at a limit of <1.

In another aspect, the invention features a method of preventing pre-cachexia, the method involving administering to the subject a cannabinoid wherein said cannabinoid is administered prior to the start of the chemotherapy treatment cycle, is administered during the treatment cycle and is optionally continued after the chemotherapy treatment cycle has been terminated.

In a specific embodiment, administration of the cannabinoid is continued for 1, 2, 3, 4, 5 weeks or more after chemotherapy is terminated. Specifically, cannabinoid administration can be continued for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 days or more after termination of chemotherapy.

In another aspect, the invention features a method of inhibiting the progression of pre-cachexia to cachexia in a subject, the method involving administering to the subject a cannabinoid wherein said cannabinoid is given prior to the start of the chemotherapy treatment cycle, is administered during the treatment cycle and is optionally continued after the chemotherapy treatment cycle has been terminated.

In another aspect, the invention features a method of treating or preventing undesirable muscle or fat loss in a cancer patient, the method involving administering to the subject a cannabinoid wherein said cannabinoid is administered prior to the start of the chemotherapy treatment cycle, is administered during the treatment cycle and is optionally continued after the chemotherapy treatment cycle has been terminated.

DETAILED DESCRIPTION OF THE INVENTION

As used herein, the terms "a", "an" and "the" are used herein to refer to one or more than one, i.e. to at least one.

As used herein, the term "cannabinoid" refers to but is not limited to a chemical compound that acts on cannabinoid receptors in cells that repress neurotransmitter release in the brain. Ligands for these receptor proteins include endocannabinoids produced naturally in the body by humans and animals, phytocannabinoids found in cannabis and some other plants and synthetic cannabinoids. The most notable cannabinoid is the phytocannabinoid tetrahydrocannabinol (THC), the primary psychoactive compound in cannabis. Cannabidiol (CBD) is another major constituent of the plant. There are at least 113 different cannabinoids isolated from cannabis, exhibiting varied effects.

Synthetic cannabinoids encompass a variety of distinct chemical classes: the classical cannabinoids structurally related to THC, the nonclassical cannabinoids (cannabimimetics) including the aminoalkylindoles, 1,5-diarylpyrazoles, quinolines, and arylsulfonamides, as well as eicosanoids related to the endocannabinoids.

According to an embodiment of the invention, the cannabinoid is selected from natural, modified or synthetic cannabinoids, specifically it is selected from the group of cannabidiol (CBD), 9-tetrahydrocannabinol, 8-tetrahydrocannabinol, (+)-1,1-dimethylheptyl analog of 7-hydroxy-delta-6-tetrahydrocannabinol, 3-(5'-cyano-1,1'-dimethylpentyl)-1-(4-N-morpholinobutyryloxy) delta 8-tetrahydrocannabinol hydrochloride, dexanabinol, nabilone, levonantradol, N-(2-hydroxyethyl) hexadecanamide, delta-8-tetrahydrocannabinol or any active metabolite, derivative or analogue thereof.

Specifically, nabilone is used according to the invention.

Specifically, Canemes® is used according to the invention, which contains the active ingredient nabilone. Canemes® is formulated as capsules, containing 1 mg Nabilone.

As an alternative, capsules may be used that contain 0.25 mg Nabilone as active ingredient.

Unless otherwise specifically defined, the term "analogs", "metabolites" or "derivatives" refers to compounds that have the same properties as cannabinoids, i.e. said analogues, metabolites and derivatives of cannabinoids act on the same cannabinoid receptor and have similar effect on said receptor as the cannabinoid the respective analogues, metabolites and derivatives are derived from. For example, the analogs can also act on cannabinoid receptors in cells that alter neurotransmitter release in the brain.

Unless otherwise specified, cannabinoids also encompass analogs, derivatives and metabolites therefrom as defined above.

According to embodiments of the present invention, the term "a cannabinoid" also encompasses combinations or mixtures of 1, 2, 3, 4, 5, 6, 7, 8, 9, 10 or more different cannabinoids or a plurality of different cannabinoids of different origin and any combinations or mixtures, optionally also in combination with further active agents, compounds or pharmaceutical excipients.

The term "low dose" according the present invention means the amount of a cannabinoid up to 10 mg/day administered to a subject. Specifically, the cannabinoid low dose can contain any mg of amounts of a cannabinoid, for example 0.1, 0.5, 1, 1.5, 2, 2.5, 3, 3.5, 4, 4.5, 5, 5.5, 6, 6.5, 7, 7.5, 8, 8.5, 9, 9.5, 10 mg per day.

Low dose nabilone according the present invention specifically refers to an amount of up to 10 mg/day administered to a subject. Specifically, nabilone low dose refers to 0.1, 0.5, 1, 1.5, 2, 2.5, 3, 3.5, 4, 4.5, 5, 5.5, 6, 6.5, 7, 7.5, 8, 8.5, 9, 9.5, 10 mg per day. Specifically a low dose range is from >0.5 mg/day to <10 mg/day, specifically from 1 to 5 mg/day.

The term "very low dose" according the present invention means the maximum amount of a cannabinoid of 0.5 mg/day administered to a subject. Specifically, the cannabinoid very low dose can contain 0.1, 0.15, 0.2, 0.25, 0.3, 0.35, 0.4, 0.45, 0.5, mg per day. Specifically a very low dose contains 0.1 to 0.5 mg/day, specifically it contains 0.25 to 0.5 mg/day specifically it is about 0.25 mg/day or about 0.5 mg/day. Optimal dosing can be determined by the skilled artisan by evaluating, amongst other factors, efficacy and safety.

Very low dose nabilone refers to 0.5 mg nabilone/day administered to a subject. Specifically, nabilone very low dose refers to 0.1, 0.15, 0.2, 0.25, 0.3, 0.35, 0.4, 0.45, 0.5, mg per day. Specifically a very low dose of nabilone is in the range of 0.1 to 0.5 mg/day, specifically in the range of 0.25 to 0.5 mg/day, specifically it is about 0.25 mg/day or about 0.5 mg/day.

According to the embodiment, the cannabinoid dose can be varied during the treatment, e.g. a cannabinoid dose of 0.25 mg for about 1 to 4 weeks is followed by a dose of 0.5 mg. Dosage may be determined by the skilled person according to the subject's needs.

The term "treatment" relates to any treatment which improves the health status, reduces or inhibits unwanted weight loss and/or prolongs and/or increases the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

As used herein, "preventing" or "prevention" of a disease, disorder or condition refers to the reduction of the occurrence of the disorder or condition in a treated subject relative to an untreated control subject, or delays the onset or reduces the severity of one or more symptoms of the disorder or condition relative to the untreated control subject. Here, the condition specifically refers to pre-cachexia and cachexia.

The terms "protect", "prevent", "prophylactic", "preventive", or "protective" relate to the prevention and/or treatment of the occurrence and/or the propagation of a disease, e.g. cachexia or pre-cachexia, in an individual. For example, a prophylactic administration of a cannabinoid according to the present invention can protect the receiving individual from the development of pre-cachexia or cachexia. For example, a therapeutic administration of a cannabinoid, e.g. by administering a composition of the present invention, can stop the development of unwanted weight loss, e.g. inhibits pre-cachexia or cachexia.

As used herein, a "subject" means a human or animal (in the case of an animal, can be, but is not limited to, a non-human animal or mammal). A "subject" mammal can include, but is not limited to, a human or non-human mammal, such as a primate, bovine, equine, canine, ovine, feline, or rodent. In one aspect, the subject is a human. It is understood that an adult human is typically about 70 kg, and a mouse is about 20 g, and that dosing from a mouse or other non-human mammal can be adjusted to a 70 kg human by a skilled person without undue experimentation.

The route of administration can be oral, nasal, rectal, topical, intravenous, intramuscular, subcutaneous, sublingual, intrathecal, intraperitoneal, intra-articular or intradermal. It may also be by an implant for continuous release of the agent.

The cannabinoids can be formulated as a feed, a food, a liquid, an elixir, an aerosol, a spray, a tablet, a capsule, sprinkles, a gel, a nanosuspension, a nanoparticle, a microgel, a cream, an ointment, a suppository, a patch or any other form that is applicable for administering a cannabinoid.

In a specific embodiment the cannabinoid can be formulated for oral administration, like a capsule, specifically as a soft gel capsule or a syrup. It can be formulated for immediate release or sustained release.

In another embodiment, the cannabinoid is specifically suitable for inhalation or for smoking.

Specifically, administration can be oral, specifically on a daily basis. Administration, however, may also be several times per day or there may be an administration interval of 2, 3, 4, 5, 6 or more days depending on the formulation of the respective cannabinoid. Oral administration can be as morning dose on empty stomach or later in the day, specifically after eating. Administration on empty stomach may not result in any side effects.

The cannabinoid can be an active agent of a pharmaceutical formulation. The pharmaceutical composition may further comprise a pharmaceutically acceptable carrier or excipient. As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier is selected for administration by the selected route of administration. The use of such media and agents for pharmaceutically active substances is well known in the art (Rowe R. C. et al, Handbook of Pharmaceutical Excipients, 2012, 7th edition, Pharmaceutical Press, London UK). Except insofar as any conventional media or agent is incompatible with the active compound, use thereof in the pharmaceutical compositions of the invention is contemplated.

Non-limiting pharmaceutically suitable materials that may be incorporated in pharmaceutical preparations of the present invention include solubilizing/diluting agents, antioxidants, enteric coatings, absorption enhancers, pH adjusting agents and buffers, dispersing agents, coatings, antibacterial and antifungal agents, absorption delaying agents, osmolarity adjusters, isotonic agents, preservative agents, stabilizers, surfactants, thickening agents, solvents, co-solvents, emollients, coloring agents, wetting agents and ligands/pilote/targeting molecules. Methods for preparing appropriate formulations are well known in the art.

In cases where parenteral administration is elected as the route of administration, pharmaceutical compositions of the present invention may be provided to patients in combination with additional pharmaceutically acceptable sterile aqueous or non-aqueous solvents, suspensions or emulsions. Formulations to be used for in vivo administration are preferably sterile. This is readily accomplished, for example, by filtration through sterile filtration membranes.

Pharmaceutically acceptable carriers for parenteral formulations include sterile aqueous solutions or dispersions and sterile powders for the extemporaneous preparation of sterile injectable solutions or dispersion. Aqueous solvents include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils.

Intravenous vehicles may include fluid and nutrient replenishers, electrolyte replenishers, such as those based upon Ringer's dextrose, and the like.

Formulations suitable for oral administration can consist of liquid solutions, such as an effective amount of active agent(s) suspended in diluents/solubilizers, such as water, vegetable or animal oils, saline or PEG 400; capsules such as soft shell capsules, sachets or tablets, each containing a predetermined amount of the active ingredient, as liquids, solids, granules or gelatin; suspensions in an appropriate liquid; and suitable emulsions.

Aqueous solutions suitable for oral use are prepared by dissolving the active compound(s) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. Examples of non-aqueous solvents are alcohol, benzyl benzoate, butyl alcohol, polyethylene glycol, propylene glycol, N,N-dimethylacetamide, ethyl oleate, oleyl oleate, glyceryl trioleate, glyceryl dioleate, glyceryl monooleate, cetyl alcohol, stearyl alcohol, capric acid, undecenoic acid, undecanoic acid, lauric acid, oleic acid, synthetic glycerides of saturated fatty acids with 8 to 12 carbon atoms, polyoxyethylene derivatives of glycerol, bees' wax, glycerin, mineral oil, vegetable oil such as but not limited to corn oil, cottonseed oil, peanut oil, canola oil, sesame oil, safflower oil, soybean oilarachis oil, castor oil, linseed oil, soya bean oil, sunflower seed oil, olive oil, fish liver oil, and any combination thereof.

Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

In an embodiment, pharmaceutical compositions of the present invention may be provided to subjects in an encapsulated form such as a soft shell encapsulation.

Enteric coatings can further be used on capsules of the present invention to resist prolonged contact with the strongly acidic gastric fluid, but dissolve in the mildly acidic or neutral intestinal environment. Without being so limited, cellulose acetate phthalate, Eudragit™ and hydroxypropyl methylcellulose phthalate (HPMCP) can be used in enteric coatings of pharmaceutical compositions of the present invention.

Cellulose acetate phthalate concentrations generally used are 0.5-9.0% of the core weight. The addition of plasticizers improves the water resistance of this coating material, and formulations using such plasticizers are more effective than when cellulose acetate phthalate is used alone. Cellulose acetate phthalate is compatible with many plasticizers, including acetylated monoglyceride; butyl phthalybutyl glycolate; dibutyl tartrate; diethyl phthalate; dimethyl phthalate; ethyl phthalylethyl glycolate; glycerin; propylene glycol; triacetin; triacetin citrate; and tripropionin. It is also used in combination with other coating agents such as ethyl cellulose, in drug controlled-release or time-release preparations.

According to a specific embodiment, a composition comprising nabilone and randomly methylated B cyclodextrin (RAMEB) in the weight ratio (dry weight to dry weight) of 1:60-1:140 as described in detail in EP2643022 is used, wherein nabilone and RAMEB are comprised as an aqueous soluble complex.

Pharmaceutical preparations containing cannabinoids are well known in the art. For example, but not limited thereto it can be Sativex, a mouth spray with natural extracts of the cannabis plant; Dronabinol, a synthetic Delta-9 THC; Nabilone; Dexanabinol, a synthetic cannabinoid; CT-3 (ajulemic acid), a synthetic analog of the THC metabolite THC-11-oic acid; HU308, a synthetic chemical compound composed of central cannabinoid (CB1), peripheral cannabinoid (CB2), and non-CB receptor-mediated pharmacology; Rimonabant/Acomplia, ayntheic chemical that blocks endocannabinoids from being received in the brain; Taranabant/MK-0364, which targets receptors in the brain linked to appetite; acts as a Cannabinoid receptor type 1 (CB1R) inverse agonist; Canemes®, containing nabilone as active ingredient.

The term "pre-cachexia" is currently defined as a pathological state necessitating intervention (e.g. Fearon K. et al., Lancet Oncol, 2011, Vol. 12(5), 489-495). Accordingly, pre-cachexia encompasses the early pathophysiologic state of normal tissue wasting or atrophy which does not yet meet the clinical criteria for cachexia.

"Pre-cachexia" or "early cachexia" is defined based on the presence of one, two, three or all of to the following criteria:
 (a) underlying chronic disease; specifically cancer;
 (b) unintentional weight loss >1 kg but <5% of usual body weight during the last 6 months;
 (c) chronic or recurrent systemic inflammatory response;
 (d) anorexia or anorexia-related symptoms; and
 (e) a Glasgow prognostic score lower than 2.

Pre-cachexia or early cachexia may include therefore patients with a chronic disease, small weight loss, and a chronic or recurrent systemic inflammatory disease and/or anorexia.

Pre-cachexia may be determined by using one of the following parameters:

For example, a subject may be pre-cachectic when the subject's weight is stable or when the subject's weight loss is about 1%, 1.5%, 2%, 2.5%, 3%, 3.5%, 4% or 4.5% of the body weight and the Glasgow prognostic score is >0 and <2.

"Cachexia" is a condition often but not exclusively associated with cancer, which is manifested in weight loss, of at least 5% or more of body weight. A universal definition of cachexia is provided in Fearon K. et al., 2011 and in Blum D. et al., 2014. In general, cachexia refers to the progressive loss of lean body mass (particularly of muscle mass) that typically is associated with gross body weight loss that is at least 5, 6, 7, 8, 9, 10% or more and a Glasgow prognostic score of >2. Muscle and adipose tissue loss, indicative of cachexia, may be detected by a computed tomography (CT) scan (Martin et al, J. et al., 2013, Clin Oncol 31: 1539-1547).

Cachexia may be determined by using CASCO calculation as described above. CASCO may therefore be calculated as follows (Argiles et al., 2011).

In some embodiments, cachexia in a subject results in reduced protein reserves, decreased strength and functional capacity, frailty, falls, reduced aerobic capacity, reduced energy requirements or increased mortality in patients and the methods of this invention serve to prevent these conditions.

In some embodiments, cachexia in a subject results in increased dietary protein needs, inflammation (accelerated muscle protein breakdown), loss of motor units (aging CNS), reduced rate of muscle protein synthesis (post-prandial), and/or changing endocrine function (testosterone, estrogen, growth hormone, insulin resistance).

According to an embodiment of the invention, cachexia is characterized by the presence of one or more of the following criteria:
a) weight loss >5% the last 6 months,
b) weight loss >2% the last 6 months and a BMI <20 kg/m$^2$,
c) increased serum concentration of C-reactive protein (CRP), and optionally together with any of the following
a) progressive loss of both fat and skeletal muscle,
b) refractoriness of weight loss to increased nutritional input,
c) elevated resting energy expenditure (REE),
d) decreased protein synthesis,
e) altered carbohydrate metabolism,
f) hyper-catabolism of muscle via the ATP-ubiquitin-proteasome pathway of proteolysis,
g) increased degradation of adipose tissue via lipolysis,
h) asthenia,
i) anemia,
j) chronic fatigue,
k) nausea,
l) loss of bone mass,
m) a Glasgow prognostic score >2, i.e. C-reactive protein >10 mg/l and albumin <35 g/l.

"Cancer-induced cachexia" characterizes cachexia associated with the presence of a cancer or tumor.

As used herein, the term "chemotherapy" refers to any treatment using chemotherapeutic drugs which usually are rather non-specific intracellular poisons, especially related to inhibiting the process of cell division. Chemotherapy is typically given in cycles, which is a treatment followed by a period of rest. A cycle can last one or more days, but is usually one, two, three, or four weeks long. A course of chemotherapy is comprised of multiple cycles. Each course is different, but generally consists of four to six cycles. Chemotherapy as used herein can either encompass one cycle, but also can include two or more treatment cycles.

Chemotherapeutic agents can be drugs or cytotoxic agents that inhibit or prevent the function of cells and/or causes destruction of cells. The drugs or cytotoxic agents may be targeted, or systemically administered.

Examples of cytotoxic agents include radioactive isotopes, chemotherapeutic agents, and toxins such as small molecule toxins or enzymatically active toxins of bacterial, fungal, plant or animal origin, including synthetic analogues and derivatives thereof. The cytotoxic agent may be selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid and a vinea alkaloid or a combination of two or more thereof.

In one embodiment the drug is a chemotherapeutic agent selected from the group consisting of a topoisomerase inhibitor, an alkylating agent (eg. nitrogen mustards; ethylenimes; alkylsulfonates; triazenes; piperazines; and nitrosureas), an antimetabolite (eg. mercaptopurine, thioguanine, 5-fluorouracil), an antibiotics (eg. anthracycines, dactinomycin, bleomycin, adriamycin, mithramycin) a mitotic disrupter (eg. plant alkaloids—such as vincristine and/or microtubule antagonists—such as paclitaxel), a DNA intercalating agent (eg carboplatin and/or cisplatin), a DNA synthesis inhibitor, a DNA-RNA transcription regulator, an enzyme inhibitor, a gene regulator, a hormone response modifier, a hypoxia-selective cytotoxin (eg. tirapazamine), an epidermal growth factor inhibitor, an anti-vascular agent (eg. xanthenone 5,6-dimethylxanthenone-4-acetic acid), a radiation-activated prodrug (eg. Nitro aryl ethyl quaternary (NMQ) salts) and a bioreductive drug and a combination of two or more thereof.

The chemotherapeutic agent may be selected from the group consisting of Eiiotinib (TARCEVA®), Bortezomib (VELCADE®), Fulvestrant (FAS LODEX®), Sutent (SU 11248), Letrozole (FEMARA®), Imatinib mesylate (GLEEVEC®), PTK787/ZK 222584, Oxaliplatin (Eloxatin®), 5-FU (5-fluorouracil), Leucovorin, Rapamycin (Sirolimus, RAPAMUNE®.), Lapatinib (GSK572016), Lonafarnib (SCH 66336), Sorafenib (BAY43-9006), and Gefitinib (IRESSA®.), AG1478, AG1571 (SU 5271; Sugen) and a combination of two or more thereof.

The chemotherapeutic agent may be an alkylating agent such as thiotepa, CYTOXAN® and/or cyclophosphamide; an alkyl sulfonate such as busulfan, improsulfan and/or piposulfan; an aziridine such as benzodopa, carboquone, meturedopa and/or uredopa; ethylenimines and/or methylamylamines such as altretamine, triethylenemylamine, triethylenephosphoramide, triethylenethio-phosphoramide and/or trimethylomelamine; acetogenin such as bullatacin and/or bullatacinone; camptothecin; bryostatin; callystatin; cryptophycins; dolastatin; duocarmycin; eleutherobin; pancratistatin; sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide and/or uracil mustard; nitrosureas such as carmustine, chlorozotocin, fotemustine, fomustine, nimustine, and/or ranimustine; dynemicin; bisphosphonates such as clodronate; an esperamicin; a neocarzinostatiri chromophore; aclacinomysins, actinomycin, anthramycin, azaserine, bleomycins, cactinomycin, carabiciti, earminomycm, carzinophilin, chromomycin, dactinomycin, daunorubicin, detorubicin, 6-diazo-5-oxo-L-norleucine, ADRIAMYCIN®, doxorubicin such as morpholino-doxorubicin, cyanomorpholino-doxorubicin, 2-pyrrolino-doxorubicin and/or deoxydoxorubicin, epirubicin, esorubicin, idarubicin, marcel lomycin, mitomycins such as mitomycin C, mycophenolic acid, nogalamycin, olivomycins, depomycin, puromycin, quelamycin, rodorubicin, streptonigrin, streptozocin, tubercidin, ubenimex, zinostatin, zorabicin; anti-metabolites such as methotrexate and 5-fluorouracil (5-FU); folic acid analogues such as denopterin, methotrexate, pteropterin, trimetrexate; purine analogues such as fludarabine, 6-mercaptopurine, thioguanine; pyrimidine analogues such as ancitabine, azacitidine, 6-azauridine, carmofur, cytarabine, dideoxyuridine, doxifluridine, enocitabine, floxuridine; androgens such as calusterone, drornostanoione propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defo famine; demecolcine; diaziquone; elformithine; elliptinium acetate; an epothilone; etoglucid; gallium nitrate; hydroxyurea; lentinan; lonidamine; macrocyclic depsipeptides such as maytansine and ansamitocins; mitoguazone; mitoxantrone; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2''-trichlorotriethylamine; trichothecenes such as verracurin A, roridin A and/or anguidine; urethan; vindesine; dacarbazine; mannomustine; mitobronitol; mitolactol; pipobroman; gacytosine; arabinoside; cyclophosphamide; thiotepa; taxoids—such as TAXOL 1®, paclitaxel, abraxane, and/or TAXOTERE®, doxetaxel; chloranbucil; GEMZAR® gemcitabine; 6-thioguanine; mercaptopurine; methotrexate; platinum analogues such as cisplatin and carboplatin; vinblastine; platinum; etoposide; ifosfamide; mitoxantrone; vincristine; NAVELBiNE®, vinorelbine; novantrone; teniposide; edatrexate; daunomycin; aminopterin; xeloda; ibandronate; topoisomerase inhibitor RFS 2000; difluoromethyiomithine (DMFO); retinoids such as retinoic acid; capecitabine; and pharmaceutically acceptable salts, acids, derivatives or combinations of two or more of any of the above.

The drug may be a tubulin disruptor including but not limited to: taxanes such as paclitaxel and docetaxel, vinca alkaloids, discodermolide, epothilones A and B, desoxyepothilone, cryptophycins, curacin A, combretastatin A-4-phosphate, BMS 247550, BMS 184476, BMS 188791; LEP, RPR 109881A, EPO 906, I X D 258, ZD 6126, vinflunine, LU 103793, dolastatin 10, E7010, TI 38067 and T900607, colchicine, phenstatin, chalcones, indanocine, T138067, oncocidin, vincristine, vinblastine, vinorelbine, vinflunine, halichondrin B, ER-86526, pironetin, spongistatin 1, spiket P, cryptophycin, rhizoxin, sarcodictyin, eleutherobin, laulimalide, VP-16 and D-24851 and pharmaceutically acceptable salts, acids, derivatives or combinations of two or more of any of the above.

The drug may be a DNA intercalator including but not limited to: acridines, actinomycins, anthracyclines, benzothiopyranoindazoles, pixantrone, crisnatol, brostallicin, Cl-958, doxorubicin (adriamycin), actinomycin D, daunorubicin (daunomycin), bleomycin, idarubicin, cyclophosphamide, melphalan, mitomycin C, bizeiesin, etoposide, mitoxantrone, SN-38, carboplatin, cis-platin, actinomycin D, amsacrine, DACA, pyrazoioacridine, irinotecan and topotecan and pharmaceutically acceptable salts, acids, derivatives or combinations of two or more of any of the above.

The drug may be an anti-hormonal agent that acts to regulate or inhibit hormone action on tumours—such as anti-estrogens and selective estrogen receptor modulators, including, but not limited to, tamoxifen, raloxifene, droloxitene, 4-hydroxytamoxifen, trioxitene, keoxifene, LY1 17018, onapristone, and/or fareston toremifene and pharmaceutically acceptable salts, acids, derivatives or combinations of two or more of any of the above. The drug may be an aromatase inhibitor that inhibits the enzyme aromatase, which regulates estrogen production in the adrenal glands such as, for example, 4(5)-imidazoles, aminoglutethimide, megestrol acetate, AROMASIN®, exemestane, fadrozole, RIVISOR®, vorozole, FEMARA®, letrozole, and ARJMIDEX® and/or anastrozole and pharmaceutically acceptable salts, acids, derivatives or combinations of two or more of any of the above.

The drug may be an anti-androgen such as flutamide, nilutamide, bicalutamide, leuprolide, goserelin and/or troxacitabine and pharmaceutically acceptable salts, acids, derivatives or combinations of two or more of any of the above.

According to the terms of the invention, a "chemotherapy cycle" or "chemotherapeutic course" refers to the administration of a chemotherapeutic drug followed by a pause, thus administration occurs in blocks of time. Most chemotherapy treatments are given in repeating cycles. The length of a cycle depends on the treatment being given. Most cycles range from 2 to 6 weeks. For example, a chemotherapeutic agent is administered for two weeks followed by a rest period of one week, thus making it a 3-week cycle that can optionally be repeated. The number of treatment doses scheduled within each cycle also varies depending on the drugs being given. The determination of a chemotherapy cycle can be done by a skilled medicine according to the needs of the subject.

Maintenance of the cannabinoid administration for the duration of the chemotherapy thus refers to one or more chemotherapy cycles, each of these cycles can be of several days and up to several weeks.

Start of cannabinoid administration "immediately after diagnosis of cancer" according to the invention means a period of less than 1 week, less than 6, 5, 4, 3, 2, 1 days after the physician has informed the patient about a cancer disease.

Start of cannabinoid administration "immediately after diagnosis of relapse of cancer" according to the invention means a period of less than 1 week, less than 6, 5, 4, 3, 2, 1 days after the physician has informed the patient about the recurrence of a cancer disease.

According to an alternative embodiment, administration of the cannabinoid can start at least 4 weeks, at least 3 weeks, at least 2 weeks, at least 1 week before chemotherapy begins.

As an alternative, supplementary administration of a cannabinoid is started 30, 29, 28, 27, 26, 25, 24, 23, 22, 21, 20, 19, 18, 17, 16, 15, 14, 13, 12, 10, 9, 8, 7, 6, 5, 4, 3, 2, 1 days before chemotherapy starts.

The present invention is further illustrated by the following examples without being limited thereto.

EXAMPLES

Example 1

Prospective, single center, randomized, double-blind placebo-controlled study evaluating the effectiveness of low dose cannabinoid therapy with nabilone (Canemes®) in prophylactic treatment of cachexia in patients with verified, metastatic colorectal or metastatic pancreatic cancer. The aim of the study is the prevention of critical weight loss of more than 10% in patients with metastatic colorectal or metastatic pancreatic cancer by supplementary administration of low dose cannabinoid nabilone (Canemes®).

Patients are treated by one of following chemotherapies:
a) Palliative chemotherapy (platin-based):
Pancreatic Cancer:
Cisplatin (Cisplatin) 25 mg/m$^2$ i.v.
Gemcitabine (Gemzar) 1000 mg/m$^2$ i.v.
(day 1 and day 8, repeat on day 22—in total 8 cycles until progression)
Colorectal Cancer:
Capecitabine (Xeloda) 2500 mg/m$^2$ p.o.
(day 1-14, repeat on day 22—until disease progression) according to local standard
Arm A (control group): Placebo drug
Arm B (intervention group): supplemental administration of synthetic cannabinoid nabilone 0.25 mg capsules starting at least 7 days before start of chemotherapy, daily during first month of therapy, subsequently dose escalation to 0.5 mg in second month.

Any patient who is diagnosed with metastatic colorectal or metastatic pancreatic cancer and is eligible for chemotherapy with Cisplatin/Gemcitabine resp. Capecitabine will be stratified according to the respective assigned CTx regimen.

Patients in Arm B, the intervention group, receive additionally to the standard chemotherapy regimen 0.25 mg nabilone (Canemes®) per os continuously during the first month of therapy on a daily basis (day 1-28), administration starting at least 7 days before chemotherapy. Canemes® supplementally administered.

At start of the second month of therapy (day 29) the dosage of cannabinoids will be escalated to 0.5 mg per day.

In case of toxicities during the first 28 days of chemotherapy the dosage will remain with 0.25 mg, respectively, after day 29, maintained at 0.25 mg nabilone per day.

Subsequent re-escalation to 0.5 mg is not allowed.

Patients in Arm A, the control group, receive placebo drug in addition to the standard chemotherapy on a daily basis.

Study Endpoint:

Following parameters will be compared in the intervention group and the control group:

Primary Endpoint:

Prevention of critical weight loss of more than 10% in patients with metastatic colorectal or metastatic pancreatic cancer by supplemental administration of cannabinoid, low dose nabilone.

Secondary Endpoints:
- Bioelectrical Impedance Analysis (BIA): Determination of parameters on functional nutritional status: fat-free mass (FFM), total body water (TBW), body fat and phase angle will be evaluated by BIA (reduction of phase angle by more than 10% during treatment/observation period)
- Prevention of signs of pre-cachexia.
- Modified Glasgow Prognostic Score mGPS: determination of inflammatory parameters CRP and albumin at baseline, and subsequently during chemotherapy
- Weight loss by more than 5%, in combination with increased levels of CRP, decreased levels of albumin and depletion of skeletal muscle mass will be evaluated in order to detect signs of pre-cachexia.
- Concomitant evaluation of Charlson Comorbidity Index—CCI at baseline
- Quality of life (QoL): assessment by the Short Form 12 Health Survey Questionaire (SF-12) at baseline, and subsequently during chemotherapy Including questionnaires on quality of sleep, pain and depression/anxiety
- Toxicity during chemotherapy:
- Assessment of adverse events during treatment period until the end of chemotherapy according to Common Terminology Criteria for Adverse Events (CTCAE 4.0)
- Assessment of chronic toxicities
- Progression-free survival (PFS) from treatment start until progression or death from any cause and overall survival (OS) from treatment start until death from any cause after one year.

Study Rationale:

Malnutrition and weight loss is a relevant clinical problem in patients with metastatic colorectal or metastatic pancreatic cancer and is associated with reduced treatment tolerability and efficacy, increased toxicities and impaired quality of life.

At time of diagnosis most patients with advanced cancer already experienced unintentional weight loss (Martin L, Senesse P, Gioulbasanis I, Antoun S, Bozzetti F, Deans C, Strasser F, Thoresen L, Jagoe R T, Chasen M, Lundholm K, Bosaeus I, Fearon K, Baracos V E. Diagnostic criteria for the classification of cancer-associated weight loss. J Clin Oncol. 2015 Jan. 1; 33(1):90-9. doi: 10.1200/JCO.2014.56.1894. Epub 2014 Nov. 24) during chemotherapy patients with metastatic colorectal and especially metastatic pancreatic cancer often report a progressive decline in dietary intake due to early satiety, anxiety, depression, pain and nausea.

Cannabinoids are increasingly prescribed for gastrointestinal disorders—particularly nausea and emesis—as an appetite stimulant and for treating visceral pain (Malik Z, Baik D, Schey R. The role of cannabinoids in regulation of nausea and vomiting, and visceral pain. Curr Gastroenterol Rep. 2015 February; 17(2):429).

The aim of this study is to evaluate the efficacy of low dose supplemental cannabinoid therapy in patients with metastatic colorectal and metastatic pancreatic cancer receiving palliative platin-based chemotherapy, in order to prevent critical weight loss and signs of cachexia.

We hypothesize that weight loss by more than 10% assessed one year after start of chemotherapy, will be improved by 20% of patients in the study group receiving low dose cannabinoids—due to supplemental low dose cannabinoid therapy. This supplemental therapy will alleviate symptoms of pain, anxiety and nausea and thus result in improvement of tolerability, better quality of life and less toxicity.

Weight loss by more than 5%, in combination with increased levels of CRP, decreased levels of albumin and depletion of skeletal muscle mass will be evaluated in order to detect signs of cachexia.

By assessing nutritional status for metastatic colorectal carcinoma, clinical studies have shown that up to one third of patients already lost more than 10% of their stable body weight in the preceding 6 months before chemotherapy start. Cachexia and malnutrition present significant predictors for survival of patients with metastatic colorectal cancer, median survival for patients receiving first-line chemotherapy was indicated by 17.5 months and declines to 8.5 months receiving second-line chemotherapy and beyond. Varying indicators defining cancer cachexia in patients with metastatic colorectal cancer cachexia, such as increased CRP values, critical weight loss and decreased energy intake are often observed, signs of cachexia are claimed to range from 22% to 55% of patients—varying results occur due to deviant cancer cachexia criteria (Blauwhoff-Buskermolen S, Versteeg K S, de van der Schueren M A E, den Braver N R, Berkhof J, Langius J A E, Verheul H M W. Loss of Muscle Mass During Chemotherapy Is Predictive for Poor Survival of Patients With Metastatic Colorectal Cancer. JCO 2016; Thoresen L, Frykholm G, Lydersen S, Ulveland H, Baracos V, Prado C M M, Birdsell L, Falkmer U. Nutritional status, cachexia and survival in patients with advanced colorectal carcinoma. Different assessment criteria for nutritional status provide unequal results. Clinical Nutrition 2013; 32:65-72).

One of the most distressing factors of metastatic pancreatic cancer is distinct and progressive weight loss, a significant clinical problem during chemotherapy leading to poor tolerability and higher treatment related toxicity.

Median survival time is 6 to 10 months for patients with locally advanced pancreatic cancer, and 3 to 6 months for those with metastatic disease (Rocha Lima C M, Green M R, Rotche R, Miller Jr W H, Jeffrey M G, Cisar L A, Morganti A, Orlande N, Gruia G, Miller L L. Irinotecan Plus Gemcitabine Results in No Survival Advantage Compared With Gemcitabine Monotherapy in Patients With Locally Advanced or Metastatic Pancreatic Cancer Despite Increased Tumor Response Rate. JCO 2004: 22:3776-3783).

Randomized clinical studies in patients with metastatic pancreatic cancer indicate that 85% of patients exhibit weight loss already at time of diagnosis and this weight loss progresses until death.

When assessing pre-illness weight and duration of weight loss in 20 patients with unresectable pancreatic cancer, Wigmore et al. showed that at diagnosis all patients had lost weight, median loss of 14.2% of their pre-illness stable weight and this weight loss was progressive, increasing to a median of 24.5% by the time of their last assessment before death. 15% of patients would be classified as severely malnourished already at diagnosis, if weight loss by more than 20% indicated severe malnutrition—before death 60% of all patients would account for this category[2]. Cancer cachexia impairs prognosis and is also associated with impairment of physical function, increased psychological distress and low quality of life and occurs in up to 80% of patients with advanced pancreatic cancer (Tan B H L, Birdsell L A, Martin L, Baracos V E, Fearon K C H. Sarcopenia in an Overweight or Obese Patient Is an Adverse Prognostic Factor in Pancreatic Cancer. Clin Cancer Res 2009; 15(22)).

Study Design:

Number of patients: In total 40 patients (1:1 study drug: placebo)

The difference between the two study arms for the primary endpoint (weight loss of >10% from the start of CTx until last day of CTx) will be evaluated by means of a chi-square test.

When the sample size in each group is 20 stratification will be performed according to assigned Ctx regimen.

Inclusion Criteria:
Any patient diagnosed with metastatic pancreatic or colorectal carcinoma who is eligible for palliative chemotherapy.
Written informed consent obtained prior to any study specific screening activities and patients have to be able to comply with this protocol.
Histologically confirmed metastatic pancreatic or metastatic colorectal carcinoma treated with palliative platin-based chemotherapy.
Women of childbearing potential must have a negative pregnancy test at screening and must use effective contraception.

Exclusion Criteria:
Contraindications to the study drug (nabilone—Canemes®)
Pregnant or lactating women
History of other malignancy; yet patients who have been disease-free for 5 years or patients with a history of completely resected non-melanoma skin cancer or successfully treated in situ carcinoma are eligible
Concurrent other cancer therapy (chemotherapy, immunotherapy, anti-hormonal or biologic therapy) or concurrent treatment with an investigational drug
Serious medical or psychiatric disorders that would interfere with the patient's safety or informed consent, especially psychotic illness in patient's medical history
Participation in another interventional clinical study at time of study inclusion (except follow-up period without treatment for more than 30 days) or denial of the simultaneous participation in a non-interventional study by the PI of the study center.

Example 2

Case study evaluating the effectiveness of low dose cannabinoid therapy with nabilone (Canemes®) in prophylactic treatment of cachexia in patients with verified, metastatic colorectal cancer. The aim of the study is the prevention of critical weight loss of more than 10% in patients with metastatic colorectal cancer by supplementary administration of low dose cannabinoid nabilone (Canemes®).

Patients will be treated with chemotherapy chosen by a specialist. Additionally, after diagnosis and before chemotherapy, supplemental daily administration of synthetic cannabinoid nabilone 0.25 mg capsules is started and if necessary the dose is escalated to 0.5 mg.

Weight and inflammatory parameters (CRP and albumin) will be measured at baseline, and subsequently during chemotherapy over the period of the chemotherapy and up to six months thereafter.

Weight loss by more than 5%, in combination with increased levels of CRP and decreased levels of albumin will be evaluated in order to detect signs of pre-cachexia.

Example 3

Case study evaluating the effectiveness of low dose cannabinoid therapy with nabilone (Canemes®) in prophylactic treatment of cachexia in patients with verified, metastatic colorectal cancer. The aim of the study is the prevention of critical weight loss of more than 10% in patients with metastatic colorectal cancer by supplementary administration of low dose cannabinoid nabilone (Canemes®).

Patients will be treated with chemotherapy chosen by a specialist. Additionally, after diagnosis and before chemotherapy, supplemental daily administration of synthetic cannabinoid nabilone 0.25 mg capsules is started and if necessary the dose is escalated to 0.5 mg.

Weight will be measured at baseline, and subsequently during chemotherapy over the period of the chemotherapy and up to six months thereafter.

Weight loss by more than 5% will be evaluated in order to detect signs of pre-cachexia.

Example 4

Case study evaluating the effectiveness of low dose cannabinoid therapy with nabilone (Canemes®) in prophylactic treatment of cachexia in patients with verified, metastatic colorectal cancer. The aim of the study is the prevention of critical weight loss of more than 5% in patients with metastatic colorectal cancer by supplementary administration of low dose cannabinoid nabilone (Canemes®).

Patients will be treated with chemotherapy chosen by a specialist. Additionally, after diagnosis and before chemotherapy, supplemental daily administration of synthetic cannabinoid nabilone 0.25 mg capsules is started and if necessary the dose is escalated to 0.5 mg.

Weight will be measured at baseline, and subsequently during chemotherapy over the period of the chemotherapy and up to six months thereafter.

The invention claimed is:

1. A method of prophylactically treating pre-cachexia or cachexia in a patient suffering from cancer, comprising the step of administering a cannabinoid in an amount of 0.1 mg to 5 mg/day, wherein administration of the cannabinoid is started prior to chemotherapy and is continuously maintained for at least the duration of the chemotherapy, wherein the cannabinoid is Nabilone.

2. The method of claim 1, wherein said cannabinoid is administered in an amount of 0.25 mg to 0.5 mg/day.

3. The method of claim 1, wherein said cannabinoid is formulated for oral, inhalative or parenteral delivery.

4. The method of claim 3, wherein the oral formulation is in the form of a tablet, a capsule, a sachet, sprinkles, or a suspension.

5. The method of claim 1, wherein the cancer is selected from the group consisting of prostate cancer, breast cancer, small cell lung carcinoma, non-small cell lung carcinoma, colon cancer, rectum cancer, bladder cancer, kidney cancer, leukemia, mouth cancer, esophagus cancer, larynx cancer, stomach cancer, melanoma, pancreatic cancer, endometrial cancer, uterine sarcoma, ovarian cancer, testicular cancer, multiple myeloma, brain tumor, thyroid cancer, Hodgkin's lymphoma, non-Hodgkin's lymphoma liver cancer, gastric cancer, sarcoma osteosarcoma, acute non-lymphocytic leukemia and glioma.

6. The method of claim 1, wherein the pre-cachexia is characterized by a weight loss of >1 kg and <5% of the patient's weight compared to the weight before the start of a chemotherapy treatment cycle.

7. The method of claim 1, wherein the cachexia is characterized by a weight loss of >5% of the patient's weight compared to the eight before the start of a chemotherapy treatment cycle.

8. The method of claim 1, wherein the patient further suffers from one or more of the following conditions:
 a) progressive loss of both fat and skeletal muscle,
 b) refractoriness of weight loss to increased nutritional input,
 c) elevated resting energy expenditure (REE),
 d) decreased protein synthesis,
 e) altered carbohydrate metabolism,
 f) hyper-catabolism of muscle via the ATP-ubiquitin-proeasome pathway of proteolysis,
 g) increased degradation of adipose tissue via lysis,
 h) asthenia,
 i) anemia,
 j) chronic fatigue,
 k) nausea,
 l) loss of hone mass, and
 m) a Glasgow prognostic score lower than 2.

9. The method of claim 1, wherein administration is started immediately after a first, diagnosis of cancer or immediately after a diagnosis of relapse of cancer disease.

10. The method of claim 1, wherein administration starts at least 1 week before chemotherapy.

11. The method of claim 1, wherein the cannabinoid is continuously administered from the beginning until the end of a complete chemotherapy treatment.

12. The method of claim 1, wherein weight loss of the patient after one chemotherapy treatment cycle is less than 15%, less than 10%, less than 5%, less than 2.5%, less than 2%, or less than 1% compared to the weight of the patient before the start of a chemotherapy treatment cycle.

13. The method of claim 1, wherein C-reactive protein levels of the patient are less than 10 mg/l and albumin levels are higher than 35 g/l.

14. The method of claim 4, wherein the oral formulation is a slow release formulation.

15. The method of claim 10, wherein administration starts at least 2 weeks before chemotherapy.

16. The method of claim 10, wherein administration starts at least 3 weeks before chemotherapy.

17. The method of claim 1, wherein the cannabinoid is continuously administered for up to 12 months after termination of chemotherapy.

18. The method of claim 1, wherein said cannabinoid is administered in an amount of 0.25 rag to 5 mg/day.

\* \* \* \* \*